(12) United States Patent
Corey et al.

(10) Patent No.: US 8,324,181 B2
(45) Date of Patent: Dec. 4, 2012

(54) MODULATION OF GENE EXPRESSION BY OLIGOMERS TARGETED TO CHROMOSOMAL DNA

(75) Inventors: David R. Corey, Dallas, TX (US);
David S. Shames, Dallas, TX (US);
Bethany A. Janowski, Dallas, TX (US);
John D. Minna, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 131 days.

(21) Appl. No.: 12/750,201

(22) Filed: Mar. 30, 2010

(65) Prior Publication Data
US 2011/0207217 A1    Aug. 25, 2011

Related U.S. Application Data

(62) Division of application No. 11/599,566, filed on Nov. 13, 2006, now Pat. No. 7,709,456.

(60) Provisional application No. 60/738,103, filed on Nov. 17, 2005.

(51) Int. Cl.
*A61K 31/70* (2006.01)
*C07H 21/04* (2006.01)

(52) U.S. Cl. .......................... 514/44; 536/24.5

(58) Field of Classification Search ............... None
See application file for complete search history.

(56) References Cited

U.S. PATENT DOCUMENTS

| | | | | |
|---|---|---|---|---|
| 5,859,221 | A | 1/1999 | Cook et al. | 536/23.1 |
| 5,877,160 | A | 3/1999 | Harper et al. | 514/44 |
| 6,506,559 | B1 | 1/2003 | Fire et al. | 435/6 |
| 6,673,611 | B2 | 1/2004 | Thompson et al. | 435/455 |
| 6,867,349 | B2 | 3/2005 | Ekker et al. | 800/21 |
| 2003/0143732 | A1 | 7/2003 | Fosnaugh et al. | 435/325 |
| 2003/0165934 | A1 | 9/2003 | Elledge et al. | 435/6 |
| 2004/0259097 | A1 | 12/2004 | De Backer et al. | 435/6 |
| 2004/0259247 | A1 | 12/2004 | Tuschl et al. | 536/24.5 |
| 2005/0032733 | A1 | 2/2005 | McSwiggen et al. | 514/44 |
| 2005/0171039 | A1 | 8/2005 | McSwiggen et al. | 514/44 A |
| 2006/0205635 | A1 | 9/2006 | Corey et al. | 514/44 |
| 2007/0111963 | A1 | 5/2007 | Corey et al. | 514/44 |

FOREIGN PATENT DOCUMENTS

| | | |
|---|---|---|
| CA | 2604532 | 10/2006 |
| WO | WO 01/75164 | 10/2001 |
| WO | WO 01/83793 | 11/2001 |
| WO | WO 02/060919 | 8/2002 |
| WO | WO 03/070918 | 8/2003 |
| WO | WO 2006/113246 | 10/2006 |
| WO | WO 2006/130201 | 12/2006 |
| WO | WO 2007/086990 | 8/2007 |

OTHER PUBLICATIONS

Affymetrix/Cold Spring Harbor Laboratory ENCODE Transcriptome Project, "Post-transcriptional processing generates a diversity of 5'-modified long and short RNAs," *Nature*, 457:1028-1032, 2009.

Braasch et al., "RNA interference in mammalian cells by chemically-modified RNA," *Biochemistry*, 42:7967-7975, 2003.
Buskirk et al., "In vivo evolution of an RNA-based transcriptional activator," *Chem. Biol.*, 10:533-40, 2003 (Abstract).
Check, "RNA interference: hitting the on switch," *Nature*, 448(7156):855-858, 2007.
Corey, "RNA learns from antisense," *Nat. Chem. Biol.*, 3:8-11, 2007.
Czauderna et al. "Structural variations and stabilising modifications of synthetic siRNAs in mammalian cells," *Nucleic Acids Res.*, 31(11):2705-2716, 2003.
Elmén et al., "Locked nucleic acid (LNA) mediated improvements in siRNA stability and functionality," *Nucleic Acids Res.*, 33(1):439-447, 2005.
Ferrandina et al., "Expression of cyclooxygenase-2 (COX-2), receptors for estrogen (ER), and progesterone (PR), p53, ki67, and neu protein in endometrial cancer," *Gynecol Oncol.*, 98:383-9, 2005 (Abstract).
Gingeras, "Origin of phenotypes: genes and transcripts," *Genome Res.*, 17:682-690, 2007.
Han et al., "Promoter-associated RNA is required for Rna-directed transcriptional gene silencing in human cells," *Proc. Natl. Acad. USA*, 104:12422-12427, 2007.
Janowski et al., "Activating gene expression in mammalian cells with promoter-targeted duplex RNAs," *Nat. Chem. Biol.*, 3:166-173, 2007.
Janowski et al., "Inhibiting gene expression at transcription start sites in chromosomal DNA with antigene RNAs," *Nature Chemical Biology*, 1:216-22, 2005.
Janowski et al., "Inhibiting transcription of chromosomal DNA with antigene peptide nucleic acids," *Nat Chem. Biol.*, 1(4):210-215, 2005.
Janowski et al., "Involvement of AGO1 and AGO2 in mammalian transcriptional silencing," *Nat. Struc. Mol. Biol.*, 13:787-792, 2006.
Kaihatsu, "Recognition of chromosomal DNA by PNAs," *Chemistry & Biology*, 11:749-758, 2004.
Kawasaki and Taira, "Induction of DNA methylation and gene silencing by short interfering RNAs in human cells," *Nature*, 431:211-17, 2004.
Keen et al., "The biology of breast cancer," *Cancer*, 97(s3):825-833, 2003.
Kim et al., "Argonaute-1 directs siRNA-mediated transcriptional gene silencing in human cells," *Nat. Struct. Mol. Biol.*, 13:793-797, 2006.
Kuwabara et al., "A small modulatory dsRNA specifies the fate of adult neural stem cells," *Cell*, 116:779-793, 2004.
Leung and Whottaker, "RNA interference: from gene silencing to gene-specific therapeutics," *Pharmacol. Ther.*, 107:222-39, 2005 (Abstract).
Li et al., "Small dsRNAs induce transcriptional activation in human cells," *PNAS*, 103:17337-42, 2006.
Liu et al., "Argonaute2 is the catalytic engine of mammalian RNAi," *Science*, 305:1437-1441, 2004.

(Continued)

*Primary Examiner* — Tracy Vivlemore
(74) *Attorney, Agent, or Firm* — Parker Highlander PLLC

(57) ABSTRACT

Synthesis of a target transcript of a gene is selectively increased in a mammalian cell by contacting the cell with a polynucleotide oligomer of 12-28 bases complementary to a region within a target promoter of the gene under conditions whereby the oligomer selectively increases synthesis of the target transcript.

19 Claims, No Drawings

OTHER PUBLICATIONS

Long-Cheng et al., "Small interfering RNA directed transcriptional activation in human cells," *Proceedings of the Annual Meeting of the American Association for Cancer Research*, New York, New York, 46:1436, 2005.

Meister et al., "Human Argonaute2 mediates RNA cleavage targeted by miRNAs and siRNAs," *Mol. Cell.*, 15:185-197, 2004.

Morris et al., "Small interfering RNA-induced transcriptional gene silencing in human cells," *Science*, 305:1289-92, 2004.

Office Action, issued in U.S. Appl. No. 11/599,566, mailed Jul. 9, 2008.

Office Action, issued in U.S. Appl. No. 11/599,566, mailed Sep. 30, 2008.

Office Action, issued in U.S. Appl. No. 11/599,566, mailed Feb. 24, 2009.

Office Action, issued in U.S. Appl. No. 11/599,566, mailed Aug. 5, 2009.

Office Action issued in U.S. Appl. No. 11/376,483, mailed Mar. 31, 2008.

Office Action issued in U.S. Appl. No. 11/376,483, mailed Jun. 5, 2008.

Office Action issued in U.S. Appl. No. 11/376,483, mailed Oct. 16, 2009.

Park et al., "Double-stranded siRNA targeted to the huntingtin gene does not induce DNA methylation," *Biochem. Biophys. Res. Comm.*, 323:275-280, 2004.

Paroo and Corey, "Challenges for RNAi in vivo," *Trends Biotechnol.*, 22:390-394, 2004.

Pulukuri and Rao, "Small interfering RNA directed reversal of urokinase plasminogen activator demethylation inhibits prostate tumor growth and metastasis," *Cancer Res.*, 67:6637-6646, 2007.

Riken Genome Exploration Research Group and Genome Science Group (Genome Network Project Core Group) and the FANTOM Consortium, "Antisense transcription in the mammalian transcriptome," *Science*, 309(5740):1564-1566, 2005.

Schwartz et al., "Antisense transcripts are targets for activating small RNAs," *Nature Structural & Molecular Biology*, 15:842-8, 2008.

Suzuki et al., "Prolonged transcriptional silencing and CpG methylation induced by siRNAs targeted to the HIV-1 promoter region," *J. RNAi Gene Silencing*, 1:66-78, 2005.

Takai and Jones, "Comprehensive analysis of CpG islands in human chromosomes 21 and 22," *Proc Natl Acad Sci USA*, 99:3740-3745, 2002.

Takai and Jones, "The CpG island searcher: a new WWW resource," *In Silico Biol.*, 3:235-240, 2003.

The ENCODE Project Consortium, "Identification and analysis of functional elements in 1% of the human genome by the ENCODE pilot project," *Nature*, 447:799-816, 2007.

The FANTOM Consortium, "The transcriptional landscape of the mammalian genome," *Science*, 309:1559-1563, 2005.

Ting et al., "Short double-stranded RNA induces transcriptional gene silencing in human cancer cells in the absence of DNA methylation," *Nature Genetics*, 37:606-10, 2005.

U.S. Appl. No. 12/246,421, entitled "Modulating Gene Expression with agRNA and Gapmers Targeting Antisense Transcripts," by Jacob C. Schwartz et al., filed Oct. 6, 2008.

U.S. Appl. No. 61/058,909, entitled "Endogenous Small RNA Targets Gene Promoters in Mammalian Cells," by David R. Corey et al., filed Jun. 4, 2008.

Wahlestedt, "Natural antisense and noncoding RNA transcripts as potential drug targets," *Drug Discovery Today*, 11(11-12):503-508, 2006.

Zhang et al., "Reduction of liver Fas expression by an antisense oligonucleotide protects mice from fulminant hepatitis," *Nature Biotech.*, 18:862-867, 2000.

Zhang et al., "Regulation of endothelial nitric oxide synthase by small RNA," *Proc. Natl. Acad. Sci USA*, 102:16967-16972, 2005.

Li et al., "Small interfering RNA directed transcriptional activation in human cells," Proc Amer Assoc Cancer Res 46: 1436. Abstract 6105. Apr. 1, 2005.

Office Action issued in Australian Application No. 2006/336624, mailed Jun. 23, 2010.

Office Action issued in Canadian Application No. 2,629,664, mailed Apr. 30, 2010.

Office Action issued in Canadian Application No. 2,629,664, mailed May 3, 2011.

Office Action issued in European Application No. 06,849,880.7, mailed Mar. 24, 2011.

Office Action issued in Japanese Application No. 2008-541255, mailed Mar. 29, 2011.

Ristimäki et al., "Prognostic significance of elevated cyclooxygenase-2 expression in breast cancer," *Cancer Research* 62(3): 632-635. Feb. 1, 2002.

Sutcliffe and Brehm, "Of flies and men: p53, a tumour suppressor," *FEBS Letters* 567: 86-89. 2004.

Mollegaard et al., "Peptide nucleic acid DNA strand displacement loops as artificial transcription promoters," *Proc. Natl. Acad. Sci. USA*, 91:3892-3895, 1994.

Mori et al., "A common silencer element in the SCG10 and type II NA<+> channel genes binds a factor present in nonneuronal cells but not in neuronal cells," *Neuron*, 9:45-54, 1992.

Office Communication issued in European Patent Application No. 06849880.7, dated Dec. 15, 2011.

Office Communication issued in Japanese Patent Application No. 2008-541255, dated Nov. 22, 2011.

Wang et al., "Defining the peptide nucleic acids (PNA) length requirement for PNA binding-induced transcription and gene expression," *J. Mol. Biol.*, 313:933-940, 2001.

Office Communication issued in Australian Patent Application No. 2011200554, dated Aug. 15, 2011.

Beane et al., "Inhibiting gene expression with locked nucleic acids (LNAs) that target chromosomal DNA," *Biochemistry*, 46(25):7572-7580, 2007.

Janowski and Corey, "Inhibiting transcription of chromosomal DNA using antigene RNAs," *Nucleic Acids Symposium Series*, 49:367-368, 2005.

Katayama et al., "Antisense transcription in the mammalian transcriptome," *Science*, 309(5740):1564-1566, 2005.

Office Communication, issued in European Patent Application No. 08835168.9, dated Nov. 18, 2010.

Extended European Search Report issued in European Application No. 11002451.0, dated Mar. 30, 2012.

Office Action issued in Canadian Application No. 2,629,664, mailed Feb. 16, 2012.

MODULATION OF GENE EXPRESSION BY OLIGOMERS TARGETED TO CHROMOSOMAL DNA

CROSS-REFERENCE TO RELATED APPLICATIONS

This application is a divisional of U.S. patent application Ser. No. 11/599,566 filed on Nov. 13, 2006, now U.S. Pat. No. 7,709,456 which claims benefit of U.S. Provisional Application No. 60/738,103 filed Nov. 17, 2005. The entire contents of these applications are hereby incorporated by reference.

This work was made with Government support under grants awarded by the National Institutes of Health (NIGMS 60642 and 73042; and P50 CA 70907). The Government has certain rights in this invention.

FIELD OF THE INVENTION

The field of the invention is modulating gene transcript synthesis using polynucleotide oligomers targeting a promoter region of the gene.

BACKGROUND OF THE INVENTION

The ability of duplex RNA to recognize mRNA and silence gene expression through post-transcriptional RNA interference (RNAi) is widely appreciated (Tang, 2004). Short interfering RNAs (siRNAs) have become common laboratory tools for controlling gene expression and endogenously expressed microRNAs (miRNAs) participate in an expanding array of cellular pathways.

RNA-directed DNA methylation was described originally in plants (Matzke et al 2004), where it was found that RNA viruses and viroids could induce methylation in genomic DNA sequences (Massenegger et al 1994). Methylated bases were concentrated within sequences of DNA that were complementary to RNA, suggesting a sequence-specific mechanism for recognition (Pelissier and Wassenegger 2000).

In yeast, small RNAs that target centromere repeat sequences and mating type loci can silence gene expression by promoting modification of heterochromatin (Grewal and Moazed 2003; Bernstein and Allis 2005). Chromatin modifications involve methylation of histone H3 at Lysine 9 (Volpe et al 2002) and require RNA-dependent RNA polymerase (Sugiyarna et al 2005) and DNA polymerase II (Schramke et al 2005). Modification involves proteins of the RNA-induced transcriptional silencing (RITS) pathway (Verdel et al 2003) including argonaute 1 (Sigova et al 2004), a member of a protein family that is also involved in post-transcriptional silencing.

Recently, several reports have suggested that antigene RNAs (agRNAs)—short oligonucleotides that target chromosomal DNA—can also silence expression in mammalian cells. Kawasaki and Taira targeted ten duplex RNAs to sequences within the E-cadherin promoter that contained CpG dinucleotides (Kawasaki and Taira, 2004). DNA methylation was observed at all of these sites. Individual RNAs yielded only marginal reductions in E-cadherin expression but more complete silencing could be achieved if all ten RNAs were combined. A link between methylation and silencing was supported by the observation that duplex RNAs were not able to inhibit expression of E-cadherin when methyl-transferase genes DMNT1 and DMNT3B were silenced.

In a similar study, Morris and co-workers demonstrated that duplex RNAs targeting the promoter of Elongation factor 1α (EF1A) could inhibit expression (Morris et al, 2004). They observed methylation of DNA at the target sequence and that addition of the methylation inhibitor 5'-aza-2'-deoxycytidine (5-aza-dC) in conjunction with the histone deacetylase inhibitor trichostatin (TSA) reversed silencing. The studies from the Taira and Morris laboratories were significant because they provided evidence that RNA could target DNA for silencing in mammalian cells and suggested that RNA could induce DNA methylation. In the Morris study silencing by a synthetic agRNA required use of a peptide designed to promote nuclear uptake, but other studies have suggested that standard transfection procedures are adequate (Kawasaki and Taira 2004; Castanotto et al 2005; Janowski et al 2005; Ting et al 2005).

Other attempts to achieve RNA-directed methylation in mammalian cells have been less successful. Steer and coworkers tested RNAs that targeted the gene encoding Huntingtin and did not detect any methylation (Park et al 2004). No RNA-directed methylation was observed upon stable expression of double-stranded RNA in mouse oocytes (Svoboda, P. et al 2004). Rossi and colleagues used expressed short hairpin RNAs (shRNAs) to target a well-characterized CpG island within the promoter for the tumor suppressor RASSF1A (Castanotto et al 2005). They reported modest inhibition of gene expression. The methylation-specific PCR assay showed methylation, but the more complete bisulphite sequencing assay did not.

Our laboratory discovered that efficient RNA-mediated silencing of chromosomal DNA can be achieved independent of DNA methylation (Janowski et al 2005; U.S. Pat appl No. 60/661,769). We targeted transcription start sites to block expression by obstructing the initiation of transcription. A practical advantage of targeting transcription start sites is that they occur in all genes and provide a general and predictable class of target sequences; targeting transcription start sites would also be expected to block gene expression regardless of whether methylation occurs.

In contrast to other studies we observed no methylation by methylation-specific PCR or sodium bisulfite sequencing. Inhibition of methyl transferase activity using 5-azaC or an anti-methyl transferase siRNA had no effect on gene silencing, suggesting that methylation was not involved in silencing. The silencing we observed was more potent than that reported in prior studies, indicating that transcription start sites may be particularly susceptible targets for agRNAs.

Baylin and colleagues revisited transcriptional silencing of E-cadherin (Ting et al 2005). They observed efficient silencing of gene expression when two promoter-targeted duplex RNAs were used in tandem, but not when the RNAs were used individually. Baylin observed no evidence for DNA methylation.

It has been reported that siRNAs targeting the E-cadherin gene promoter can activate transcription (Li et al, 2005) in cultured breast cancer cells. Similarly, data has been presented indicating increased EF1A mRNA expression by promoter-targeted siRNA (Morris et al 2004; see FIG. 3A, first two bars). It has also been reported that nuclear localized small modulatory double-stranded (ds) RNA (smRNA) coding NRSE sequences triggered activation of transcription of NRSE genes in adult hippocampal neural stem cells (Kuwabara et al, 2004; and Kuwabara et al, 2005).

SUMMARY OF THE INVENTION

One aspect of the invention is a method of selectively increasing synthesis of a target transcript of a gene in a mammalian cell, wherein the target transcript is predetermined to be in need of increased synthesis, the method comprising the steps of: contacting the cell with a polynucleotide oligomer of 12-28 bases complementary to a region within a target promoter of the gene under conditions whereby the oligomer selectively increases synthesis of the target transcript; and detecting resultant selective increased synthesis of the target gene.

In one embodiment, the region is located between nucleotides −100 to +25 relative to a transcription start site of the gene. In further embodiments, the region is located between nucleotides −50 to +25, −30 to +17, and −15 to +10, relative to a transcription start site of the gene. In a particular embodiment, the region includes nucleotides −9 to +2 relative to a transcription start site of the gene. In a particular embodiment, the region includes a transcription start site of the gene.

In one embodiment, the target promoter is the promoter of the target transcript. In another embodiment, the target promoter is the promoter of an isoform of the target transcript. In further embodiments, the target promoter is both the promoter of the target transcript and the promoter of an isoform of the target transcript.

In one embodiment, the oligomer is selected from the group consisting of a double-stranded RNA, a DNA, a peptide nucleic acid, and a morpholino. In a particular embodiment, the oligomer is a double-stranded RNA of 18-25 bases.

In one embodiment, the oligomer comprises a nucleotide having a 2' chemical modification. In particular embodiments the oligomer comprises a serum stability-enhancing chemical modification selected from the group consisting of a phosphorothioate internucleotide linkage, a 2'-O-methyl ribonucleotide, a 2'-deoxy-2'-fluoro ribonucleotide, a 2'-deoxy ribonucleotide, a universal base nucleotide, a 5-C-methyl nucleotide, an inverted deoxyabasic residue incorporation, and a locked nucleic acid.

In one embodiment the cell is a cultured cell in vitro. In other embodiments, the cell is in situ in a host.

In one embodiment, the contacting step is free of viral transduction. In further embodiments, the contacting step is free of viral transduction, and the cell is contacted with a composition consisting essentially of the oligomer. In a further embodiment, the contacting step is free of viral transduction, and there is at least a 2-fold resultant increased synthesis of the target transcript. In another embodiment, the oligomer is a double-stranded RNA of 18-25 bases, a single region of the target promoter is targeted, and there is at least a 2-fold resultant increased synthesis of the target transcript. In another embodiment the contacting step is free of viral transduction, and the oligomer is not attached to a nuclear localization peptide.

In one embodiment, the cell is contacted with a 1-100 nanomolar concentration of the oligomer.

In one embodiment, the cell is a cancer cell and the gene encodes a protein selected from the group consisting of E-cadherin, human progesterone receptor (hPR), p53, and PTEN.

Another aspect of the invention is an isolated or synthetic polynucleotide oligomer for selectively increasing synthesis of a target transcript of a gene, the oligomer comprising a nucleotide sequence of 12-28 bases complementary to a region within a target promoter of the gene, wherein introduced into a cell comprising the gene the oligomer selectively increases transcription of the target transcript.

In one embodiment, the region is located between nucleotides −100 to +25 relative to a transcription start site of the gene. In further embodiments, the region is located between nucleotides −50 to +25, −30 to +17, and −15 to +10, relative to a transcription start site of the gene. In a particular embodiment, the region includes nucleotides −9 to +2 relative to a transcription start site of the gene. In a particular embodiment, the region includes a transcription start site of the gene.

In one embodiment, the target promoter is the promoter of the target transcript. In another embodiment, the target promoter is the promoter of an isoform of the target transcript. In further embodiments, the target promoter is both the promoter of the target transcript and the promoter of an isoform of the target transcript.

In one embodiment, the oligomer is selected from the group consisting of RNA, DNA, peptide nucleic acid, and morpholino.

In another embodiment, the oligomer is a double-stranded RNA of 18-25 bases comprising a nucleotide sequence selected from the group consisting of SEQ ID NO:1-11, and 12.

In particular embodiments, the target transcript encodes a protein selected from the group consisting of human major vault protein (MVP), human E-cadherin, human progesterone receptor (hPR), human p53, and human PTEN. In one embodiment, the cell is a cancer cell and the gene encodes a protein selected from the group consisting of E-cadherin, human progesterone receptor (hPR), p53, and PTEN.

A method of doing business comprising promoting, marketing, selling or licensing a subject invention.

DETAILED DESCRIPTION OF SPECIFIC EMBODIMENTS OF THE INVENTION

The invention provides methods and compositions for selectively increasing synthesis of a target transcript of a gene in a mammalian cell, wherein the target transcript is predetermined to be in need of increased synthesis, the method comprising the steps of contacting the cell with a polynucleotide oligomer of 12-28 bases complementary to a region within a target promoter of the gene under conditions whereby the oligomer selectively increases synthesis of the target transcript; and detecting resultant selective increased synthesis of the target gene.

The target transcript of the gene is predetermined to be in need of increased synthesis using routine methods. For example, reduced levels of a target transcript and/or protein relative to desired levels may be directly measured. Alternatively, the need for increased synthesis of a target transcript may be inferred from a phenotype associated with reduced levels of the target transcript.

In one embodiment, the region within the promoter of the gene is selected from a partially single-stranded structure, a non-B-DNA structure, an AT-rich sequence, a cruciform loop, a G-quadruplex, a nuclease hypersensitive elements (NHE), and a region located between nucleotides −100 to +25 relative to a transcription start site of the gene.

Preferred AT-rich sequences are found in stretches of DNA where local melting occurs, such as the promoters of genes where protein machinery must gain access to single-stranded regions, and preferably comprise the TATA box of the gene, and/or at least 60% or 70% A+T.

Preferred cruciform structures are formed from palindromic genomic sequences forming a hairpin structure on each strand, wherein the repeated sequences are separated by a stretch of non-palindromic DNA providing a single-stranded loop at the end of each of the hairpins of the cruciform.

Preferred G-quadruplex structures are identified in promoter regions of mammalian genes and are implicated in transcription regulation. For example the nuclease hypersensitivity element III of the c-MYC oncogene promoter is involved in controlling transcription and comprises a pyrimidine-rich and purine-rich sequences on the coding and non-coding strands, respectively, that can adopt I-motif and G-quadruplex structures, respectively. Stabilization of the G-quadruplex has been shown to lead to repression of c-MYC (see e.g. Siddiqui-Jain, 2002).

In one embodiment, the region targeted is located between nucleotides −100 to +25 relative to a transcription start site of the gene. In certain preferred embodiments of the method, the region is located on the template strand between nucleotides −30 to +17 relative to a transcription start site of the gene. In another embodiment, the region is located between nucleotides −15 to +10 relative to a transcription start site of the gene. In a further embodiment, the region includes nucleotides −9 to +2 relative to a transcription start site of the gene. In certain preferred embodiments, the region includes a transcription start site of the gene. In other embodiments, the region does not include any sequence downstream from the transcription start, e.g. the sequence is located between nucleotides −100 to +1. The oligomers used in the subject invention target genomic sequence and not mRNA.

In certain embodiments, the gene is known to encode and/or express one or more isoforms of the target transcript, and the method of the invention selectively increases synthesis of the target transcript over basal expression levels and/or control condition levels, while synthesis of the isoform(s) of the target transcript may decrease, increase, or stay the same. The target transcript and the isoform(s) may share the same promoter and/or transcription start site, or they may have different promoters and/or transcription start sites. Accordingly, in various embodiments, the target promoter is (1) the promoter of the target transcript, (2) the promoter of an isoform of the target transcript, or (3) is both the promoter of the target transcript and the promoter of an isoform of the target transcript. Numerous genes are known to express multiple isoforms; examples include p53 (Bourdon, 2005), PTEN (Sharrard and Maitland, 2000), Bcl-2-related genes (Akgul, 2004), and survivin (Caldas et al, 2005). For example, the methods can be used to increase expression of one target transcript by directing oligomers to the transcription start site of an isoform. Where synthesis of the target transcript is increased, and synthesis of the isoform is inhibited, the method effectively and selectively modulates relative isoform synthesis in the host cell. Hence, increased synthesis of predetermined desirous or underexpressed isoforms can be coupled with decreased synthesis of predetermined undesirable or overexpressed isoforms. As exemplified with p53β/p53 below, this embodiment can be used to effect a predetermined isoform switch in the host cells.

The polynucleotide oligomer is of a sequence and length sufficient to effect the requisite increase of target transcript synthesis. As used herein, the Singular forms "a," "an," and "the," refer to both the singular as well as plural, unless the context clearly indicates otherwise. For example, the term "an oligomer" includes single or plural oligomers and can be considered equivalent to the phrase "at least one oligomer." Suitable oligomers are typically 12-28 bases in length, and are complementary to a region within a target promoter of the gene (i.e. Watson-Crick binding complementarity). The oligomer may comprise any nucleic acid, modified nucleic acid, or nucleic acid mimic that can recognize DNA by Watson-Crick base-pairing. Mismatches between the oligomer and the region of the promoter being targeted, particularly more than one mis-match, often diminish the efficacy of increasing target transcript synthesis. The oligomer may be single-stranded or double-stranded (i.e. a duplex). In the case of duplex oligomers, a first strand is complementary to the region of the promoter being targeted, and the second strand is complementary to the first strand. The oligomer may target homopyrimidine sequences, homopyrimidine sequences, or mixed purine/pyrimidine sequences. A mixed purine/pyrimidine sequence contains at least one purine (the rest being pyrimidines) or at least one pyrimidine (the rest being purines). A variety of oligomers are known in the art that are capable of Watson-Crick base-pairing. In certain embodiments, the oligomer is selected from a double-stranded RNA, a DNA, a peptide nucleic acid, and a morpholino.

Double-stranded (ds) RNAs are particularly preferred oligomers because they are relatively easy to synthesize, and have been used in human clinical trials. Preferred dsRNAs have 18-25 bases complementary to the region of the promoter being targeted, and optionally have 3' di- or trinucleotide overhangs on each strand. Methods for preparing dsRNA and delivering them to cells are well-known in the art (see e.g. Elbashir et al, 2001; WO/017164 to Tuschl et al; and U.S. Pat. No. 6,506,559 to Fire et al). Custom-made dsRNAs are also commercially available (e.g. Ambion Inc., Austin, Tex.). The dsRNA used in the method of the invention may be chemically modified to enhance a desired property of the molecule. A broad spectrum of chemical modifications can be made to duplex RNA, without negatively impacting the ability of the dsRNA to selectively increase synthesis of the target transcript. In one embodiment, the dsRNA comprises one or more nucleotides having a 2' modification, and may be entirely 2'-substituted. A variety of 2' modifications are known in the art (see e.g. U.S. Pat. No. 5,859,221 to Cook et al.; U.S. Pat. No. 6,673,611 to ThompSon et al; and Czauderna et al, 2003). A preferred chemical modification enhances serum stability and increases the half-life of dsRNA when administered in vivo. Examples of serum stability-enhancing chemical modifications include phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation (see e.g. US Patent Publication No. 20050032733 to McSwiggen et al). The dsRNA may optionally contain locked nucleic acids (LNAs) to improve stability and increase nuclease resistance (see e.g. Elmen et al, 2005; and Braasch et al, 2003). Another type of modification is to attach a fluorescent molecule to the oligomer, for example, TAMRA, FAM, Texas Red, etc., to enable the oligomer to be tracked upon delivery to a host or to facilitate transfection efficiency determinations.

Methylase-dependent inhibition of transcription using antigene dsRNA targeting CpG islands has been described (2, 3). However, the method of the present invention is methylase-independent, wherein synthesis of the target transcript is increased independently of, and without requiring effective methylation (e.g. transcript synthesis still occurs if the cell is contacted with the oligomer in the presence of a methylase inhibitor). In a particular embodiment of the invention, the target region within the target promoter is not contained within a CpG island. Algorithms for identifying CpG islands in genomic sequences are known (e.g. see Takai and Jones, 2002; and Takai and Jones 2003). In another embodiment of the invention, the oligomer is a double-stranded RNA, and the target region within the target promoter does not include a CG dinucleotide.

Peptide nucleic acids (PNAs) are also preferred oligomers for use in the method of the invention. Various PNA configurations are known in the art. For example, the PNA oligomer may be homopyrimidine, optionally prepared as a bisPNA, where one PNA oligomer binds the target via Watson-Crick base pairing, and a second oligomer binds via Hoogsteen recognition (see e.g. Nielsen, 2004); homopurine, optionally substituting one or more adenines with diaminopurine (see e.g. Haaima et al, 1997); or mixed purine/pyrimidine, optionally configured to form a tail-clamp at the target sequence (see e.g. Kaihatsu et al, 2003). In a preferred embodiment, the PNA is single-stranded mixed purine/pyrimidine.

DNA oligomers can also be used in the method of the invention. However, unmodified oligodeoxynucleotides are subject to rapid degradation by nucleases. Therefore, when DNA oligomers are used, they preferably have chemical modifications to increase nuclease resistance. A variety of chemical modifications to increase nuclease resistance are known in the art. The simplest and most widely used modification is the phosphorothioate (PS) modification, in which a sulfur atom replaces a non-bridging oxygen in the oligophosphate backbone. DNA oligomers are commercially available through numerous vendors (e.g. Integrated DNA Technologies, Coralville, Iowa).

Other types of oligomers that can be used include morpholino oligomers (see e.g. Summerton and Weller, 1997) and LNAs (see e.g. Wahlestedt et al, 2000). The mammalian cell that is contacted with the oligomer can be in vitro (e.g. a cultured cell), or in situ in a host. Examples of cultured cells include primary cells, cancer cells (e.g. from cell lines), adult or embryonic stem cells, neural cells, fibroblasts, myocytes, etc. The cell can be from any mammal. In one embodiment, the cell is a human cell in vitro. In a further embodiment, the cell is a breast cancer cell and the gene is the human progesterone receptor. In other embodiments, the cell is a cancer cell and the gene encodes a protein selected from the group consisting of E-cadherin, human progesterone receptor (hPR), p53, and PTEN.

Cultured human cells commonly used to test putative therapeutics for human diseases or disorders can be used to screen oligomers that target promoter regions of genes for therapeutic affect (e.g. induction of apoptosis, cessation of proliferation in cancer cells, etc.). When the cell is in situ, the host may be any mammal, and in certain preferred embodiments is a human, or an animal model used in the study of human diseases or disorders (e.g. rodent, canine, porcine, etc. animal models).

In the contacting step, the methods used to deliver the oligomer to the cell can vary depending on the oligomer used and whether the cell is in vitro or in vivo. For cells in vitro, delivery can be accomplished by direct injection into cells. When microinjection is not an option, delivery can be enhanced in some cases by using hydrophobic or cationic carriers such as Lipofectamine™ (Invitrogen, Carlsbad, Calif.). In one embodiment of the invention, the cell is a cultured cell in vitro, the oligomer is a double-stranded RNA of 18-25 bases, and the cell is contacted with a composition comprising the oligomer and a cationic lipid. PNA oligomers can be introduced into cells in vitro by complexing them with partially complementary DNA oligonucleotides and cationic lipid (21-25). The lipid promotes internalization of the DNA, while the PNA enters as cargo and is subsequently released. Peptides such as penetratin, transportan, Tat peptide, nuclear localization signal (NLS), and others, can be attached to the oligomer to promote cellular uptake (see e.g., Nielsen, 2004; Kaihatsu et al, 2003; Kaihatsu, et al, 2004; and ref. 7). Alternatively, the cells can be permeabilized with a permeabilization agent such as lysolecithin, and then contacted with the oligomer. Viral transduction can be used to deliver oligomers to cells in vitro (e.g. lentiviral transduction, see e.g. ref 7). However, in certain embodiments of the invention, it is preferred that the contacting step is free of viral transduction. In a further preferred embodiment, the contacting step is free of viral transduction, and the oligomer is not attached to a nuclear localization peptide.

For cells in situ, cationic lipids (see e.g. Hassani et al, 2004) and polymers such as polyethylenimine (see e.g. Urban-Klein, 2005) have been used to facilitate oligomer delivery. Compositions consisting essentially of the oligomer (in a carrier solution) can be directly injected into the host (see e.g. Tyler et al, 1999; McMahon et al, 2002). In a preferred embodiment of the invention, the cell is in situ in a host, the oligomer is a double-stranded RNA of 18-25 bases, and the cell is contacted with a composition consisting essentially of the oligomer. In vivo applications of duplex RNAs are reviewed in Paroo and Corey (2004).

Typically, the methods of the invention provide at least a 1.2-fold resultant increased synthesis of the target transcript relative to control conditions and/or basal expression levels. In other embodiments, increases of at least 1.5, 1.7, 2.0, 2.5, 3.0, 3.5, or 4.0 fold are achieved. Efficient increased synthesis of the target transcript can be achieved without viral transduction; in fact, in preferred embodiments the contacting step is free of viral transduction. While multiple regions of the target promoter can be targeted, highly efficient increased synthesis of the target transcript can be achieved with dsRNA targeting just a single region of the target promoter. For example in one embodiment the oligomer is a dsRNA of 18-25 bases, there is at least a 2-fold resultant increased synthesis of the target transcript relative to control conditions and/or basal expression levels, and a single region of the target promoter is targeted. Significant increases in synthesis of the target transcript can be achieved using nanomolar or picomolar (submicromolar) concentrations of the oligomer, and it is typically preferred to use the lowest concentration possible to achieve the desired resultant increased synthesis, e.g. oligomer concentrations in the 1-100 nM range are preferred; more preferably, the concentration is in the 1-50 nM, 1-25 nM, 1-10 nM, or picomolar range.

As disclosed and exemplified herein, by exploiting a hitherto unappreciated endogenous mechanism for selective gene activation, our methods are generally applicable across a wide variety of target genes, promoter regions, oligomers, mammalian cell types and delivery conditions. While conditions whereby a given oligomer selectively activates transcription of a given target gene are necessarily confirmed empirically (e.g. pursuant to the protocols described herein), we have consistently found activating oligomers for every mammalian gene we have studied; and our data indicate that mammalian cells are generally amenable to target gene selective activation using these methods.

In the detecting step of the method, selective increased synthesis of the target transcript resulting from the oligomer contacting the cell is detected. This can be determined directly by measuring an increase in the level of the gene's mRNA transcript, or indirectly by detecting increased levels of the corresponding encoded protein compared to controls. Alternatively, resultant selective increased synthesis of the target transcript may be inferred based on phenotypic changes that are indicative of increased synthesis of the target transcript.

In another aspect of the invention, provided are polynucleotide oligomers for selectively increasing synthesis of a target transcript of a gene, the oligomer comprising a nucleotide sequence of 12-28 bases complementary to a region within a target promoter of the gene located between nucleotides −100 to +25 relative to a transcription start site of the gene. When introduced into a cell comprising the gene, the oligomer selectively increases transcription of the target transcript. In one embodiment, the target transcript encodes a protein selected from the group consisting of human major vault protein (MVP), human E-cadherin, human progesterone receptor (hPR), human p53, and human PTEN. In further embodiments, the oligomer is RNA, DNA, peptide nucleic acid or morpholino. In one embodiment, the nucleic acid oligomer is a dsRNA of 18-25 bases.

Specific gene targets and dsRNA sequences that selectively increase transcript synthesis are listed in Table 1. Only one strand (shown 5' to 3') of each dsRNA is shown. Additionally the dsRNAs had 3'-dithymidine overhangs on each strand.

TABLE 1

| Gene | Target region | dsRNA |
|---|---|---|
| MVP | −54 to −36 | UGGGCUUGGCCUGCCUUGC (SEQ ID NO: 1) |
| MVP | −82 to −64 | GGGCCCUUUAACUCCCAAG (SEQ ID NO: 2) |
| E-Cadherin | −9 to +10 | CCCCCUCUCAGUGGCGUCG (SEQ ID NO: 3) |
| hPR | −25 to −6 | GGCGUUGUUAGAAAGCUGU (SEQ ID NO: 4) |
| hPR | −29 to −10 | AGGAGGCGUUGUUAGAAAG (SEQ ID NO: 5) |
| hPR | −34 to −15 | AGAGGAGGAGGCGUUGUUA (SEQ ID NO: 6) |
| p53 | −13 to +6 | GCUAAAAGUUUUGAGCUUC (SEQ ID NO: 7) |
| p53 | −9 to +10 | AAAGUUUUGAGCUUCUCAA (SEQ ID NO: 8) |
| p53 | −7 to +12 | AGUUUUGAGCUUCUCAAAA (SEQ ID NO: 9) |
| PTEN | −13 to +6 | CGCGACUGCGCUCAGUUCU (SEQ ID NO: 10) |
| PTEN | −9 to +10 | ACUGCGCUCAGUUCUCUCC (SEQ ID NO: 11) |
| PTEN | −7 to +12 | UGCGCUCAGUUCUCUCCUC (SEQ ID NO: 12) |

In a further aspect of the invention, the invention provides a method of doing business comprising promoting, marketing, selling or licensing any of the aforementioned inventions.

EXAMPLE 1 agRNA-Induced Transcriptional Increase

MVP: Using previously described methods (Janowski et al., 2005), dsRNAs targeting the major vault protein (MVP; Lange et al, 2000) at −82 to −64 (−82/−64) relative to the transcription start site, and the p53 site (−54/−36), caused 2.9 and 3.8 fold increases respectively in MVP expression at the level of RNA and protein.

E-Cadherin: An RNA targeting the −10/+9 region of E-cadherin (referred to as EC9), caused a 1.5-2.1 increase in E-cadherin expression at the level of RNA and protein. RNAs targeting −9/+10, −13/+6 and −14/+5 caused no increase or inhibited expression and gene activation. Activation of E-cadherin expression by EC9 was observed in three independent experiments.

h-PR: We have tested twenty-one RNAs complementary to progesterone receptor (PR) (Janowski et al, 2005). Several of these efficiently blocked gene expression, but in the course of these experiments we were surprised to note that some RNAs led to small but reproducible increases in expression. To follow up these observations we reduced expression of PR to near basal levels by growing cells in media with reduced levels of serum. When cells grown under these conditions were transfected with antigene RNAs (agRNAs), significant increases in hPR expression were observed. Table 2 shows the region targeted and indicates the level of increase expression obtained from various experiments.

TABLE 2

| Region targeted | Level of Increased Expression |
|---|---|
| −9/+10 | 0.5x |
| −11/+8 | 2.0x |
| −14/+5 | 1.7x |
| −19/−1 | 1.9x |
| −22/−3 | 1.0x |
| −25/−6 | 1.7 to 4.1x |
| −29/−10 | 4.5x |
| −34/−15 | 1.5x to 4.8x |
| −44/−35 | 1.2x |

The agRNA that targets −9/+10 had previously been shown to inhibit hPR in cells grown in serum, while all the other RNAs had been inactive or had shown slight activation. These results are reproducible and are observed in normal 10% serum (conditions that activate hPR) and in 2.5% serum (serum-deprived conditions that lead to a low level of hPR expression).

p53: While targeting RNAs to the promoter for p53 we discovered another form of transcriptional modulation. Expression of the major p53 isoform was decreased (abolished), while expression of a p53 isoform having a lower apparent molecular weight was increased when we targeted the following regions: −7/+12, −9/+10, and −13/+6 relative to the transcription start site of the major isoform of p53 (see Table 1, SEQ ID NOs 7-9). This lower molecular weight p53 isoform was also recently described by others (Bourdon, et al, 2005; Rohaly et al, 2005). Altered RNA expression was confirmed by RT-PCR.

The p53 gene promoter contains alternative transcription start sites. Table 3 discloses exemplary p53 transcription start site proximate target region/oligo pairs for selectively increasing target transcript synthesis. Only one strand (shown 5' to 3') of each dsRNA is shown.

TABLE 3

| Gene | Target region | dsRNA |
|---|---|---|
| p53[1] | −13 to +6 | UGACUCUGCACCCUCCUCC (SEQ ID NO: 13) |
| p53[1] | −9 to +10 | UCUGCACCCUCCUCCCCAA (SEQ ID NO: 14) |
| p53[1] | −7 to +12 | UGCACCCUCCUCCCCAACU (SEQ ID NO: 15) |
| p53[2] | −13 to +6 | AUUACUUGCCCUUACUUGU (SEQ ID NO: 16) |
| p53[2] | −9 to +10 | CUUGCCCUUACUUGUCAUG (SEQ ID NO: 17) |
| p53[2] | −7 to +12 | UGCCCUUACUUGUCAUGGC (SEQ ID NO: 18) |

[1]Bourdon et al., 2005
[2]Lamb and Crawford, 1986

We have also observed similar upregulation of isoform expression of a second gene upon transfection of cells with duplex RNAs that target PTEN (see Table 1, SEQ ID NOs 10-12).

EXAMPLE 2

Increased Human Progesterone Receptor (hPR) Expression by Antigene PNA (agPNA) Oligomers Targeting Near the Transcription Start Site Cell Culture T47D breast cancer cells (American Type Cell Culture Collection, ATCC) are maintained at 37° C. and 5% $CO_2$ in RPMI media (ATCC) supplemented with 10% (v/v) heat-inactivated (56° C., 1 hr) fetal bovine serum (Gemini Bioproducts), 0.5% non-essential amino acids (Sigma), 0.4 units/mL bovine insulin (Sigma) and 100 units/ml penicillin and 0.1 mg/ml streptomycin (Sigma).

Lipid-Mediated Transfection of PNA PNAs are obtained as described (Kaihatsu et al, 2004). Two days before transfection (day 2), T47D cells are plated at 80,000 cells per well in 6-well plates (Costar). On the day of transfection (day 0) duplexes (200 nM) and Oligofectamine (9 µl per well, Invitrogen) is diluted in Optimem (Invitrogen) according to the manufacturers' instructions. Media is changed 24 h later (day 1). On day 3 cells are passaged 1:4 into new 6-well plates. Cells are transfected a second time on day 5. Cells are harvested day 8. hPR protein levels are evaluated by Western analysis using anti-hPR antibody (Cell Signaling Technologies).

RNA Analysis. Total RNA from treated T47D cells is extracted using trizol (TRIzol, Invitrogen). RNA is treated with deoxyribonuclease to remove contaminating DNA, and 4 µg are reverse transcribed by random primers using Superscript II RNase H-reverse transcriptase (Invitrogen).

Microscopy. Cells are imaged by confocal microscopy using a Zeiss Axiovert 200 M inverted transmitted light microscope (Carl Zeiss Microimaging). Approximations of cell height are made by tracking distances in the Z-plane using an automated program. Individual cells are chosen for observation and then the microscope is underfocused until no part of the individual cell is in focus. The underfocus position in the Z-plane is noted and then the focal plane is moved upward through the cell until it is completely out of focus. The overfocus position is noted and a crude estimate of the height (Zdimension) of the cell can be calculated.

Cellular Uptake of Biologically Active PNAs PNAs are introduced into cells by complexing them with partially complementary DNA oligonucleotides and cationic lipid. The lipid promotes internalization of the DNA, while the PNA enters as cargo and is subsequently released.

Activation of hPR Expression by agPNAs. 19-base PNAs targeting near the transcription start site (−100 to +25) of hPR, and contain C- and N-terminal lysines are prepared and transfected into cells at a concentration of 200 nm. AgPNA induced increase of hPR protein expression is measured by Western analysis.

EXAMPLE 3

VEGF-Activating agRNAs Increase Vascularization

The promoter region of the human VEGF gene has been characterized (see e.g. Tischer et al, 1991). The transcription start site is at position 2363 in the published sequence (GenBank Accession no. AF095785.1). 19-mer agRNAs fully complementary to the template strand and targeting near the transcription start site of the gene (−50 to +25, where transcription start is +1) are prepared; exemplary agRNAs are shown in Table 4 (second strand and dinucleotide overhangs not shown).

TABLE 4

| agRNA | Sequence | Location |
|---|---|---|
| hV2 | GAUCGCGGAGGCUUGGGGC (SEQ ID NO: 19) | −2/+17 |
| hV6 | GGAGGAUCGCGGAGGCUUG (SEQ ID NO: 20) | −6/+13 |
| hV7 | GGGAGGAUCGCGGAGGCUU (SEQ ID NO: 21) | −7/+12 |
| hV8 | GGGGAGGAUCGCGGAGGCU (SEQ ID NO: 22) | −8/+11 |
| hV9 | CGGGGAGGAUCGCGGAGGC (SEQ ID NO: 23) | −9/+10 |
| hV10 | GCGGGGAGGAUCGCGGAGG (SEQ ID NO: 24) | −10/+9 |
| hV11 | AGCGGGGAGGAUCGCGGAG (SEQ ID NO: 25) | −11/+8 |
| hV12 | UAGCGGGGAGGAUCGCGGA (SEQ ID NO: 26) | −12/+7 |
| hV13 | GUAGCGGGGAGGAUCGCGG (SEQ ID NO: 27) | −13/+6 |
| hV14 | GGUAGCGGGGAGGAUCGCG (SEQ ID NO: 28) | −14/+5 |
| hV15 | UGGUAGCGGGGAGGAUCGC (SEQ ID NO: 29) | −15/+4 |
| hV19 | UCGGCUGGUAGCGGGGAGG (SEQ ID NO: 30) | −19/−1 |
| hV24 | AAAAGUCGGCUGGUAGCGG (SEQ ID NO: 31) | −24/−6 |
| hV25 | UAAAAGUCGGCUGGUAGCG (SEQ ID NO: 32) | −25/−7 |
| hV30 | UUUUUAAAAGUCGGCUGGU (SEQ ID NO: 33) | −30/−12 |
| hV35 | UUUUUUUUUAAAAGUCGG (SEQ ID NO: 34) | −35/−17 |
| hV40 | CCCCCUUUUUUUUUAAAA (SEQ ID NO: 35) | −40/−22 |
| hV45 | CGCCCCCCCUUUUUUUUU (SEQ ID NO: 36) | −45/−27 |
| hV49 | CAUGCGCCCCCCCUUUUU (SEQ ID NO: 37) | −49/−31 |

The effect of the agRNAs on selectively increasing synthesis of VEGF transcripts is determined in primary human umbilical vein cells (HUVECs). Resultant selective increased synthesis of the VEGF transcript is detected inferentially from increases in cell proliferation and/or directly by measuring increases in VEGF gene transcripts relative to controls. agRNAs resulting in at least a 2-fold increase in VEGF gene transcription are evaluated in animal model and clinical studies for treatment of myocardial ischemia as described below.

Ischemic Heart Model Adenoviral vectors are constructed for of VEGF-activating agRNAs to an ischemic heart mouse model using known methods (see e.g. Zender et al, 2003; Su et al, 2002; and Su et al, 2004). CD1 mice (Charles River Breeding Laboratories) are anesthetized with 15-16 µl of 2.5% Avertin per gram of body weight by i.p. injection. After the respiration of the animal is controlled by a Small Animal Volume Controlled Ventilator (Harvard Rodent Ventilator, model 683, South Natick, Mass.), a thoracotomy incision is made in the fourth intercostal space. A surgical retractor is put in the incision to expose the heart. The anterior descending coronary artery is ligated permanently with a 6-0 nonabsorbable surgical suture to induce ischemia. $1 \times 10^{11}$ genomes of viral vectors in 50 µl of Hepes saline (pH 7.4) is injected directly to multiple sites of the myocardium on the left ventricle wall around the ischemic region. Control mice receive buffer injections. Cardiac function is assessed 4 weeks after the surgery. Left ventricular end diastolic dimension (LVDd) and end systolic dimension (LVDs) are measured. The percentage of fractional shortening (FS %) is calculated as (LVDd−LVDs)/LVDd×100.

Hearts collected after echocardiography are sectioned and stained with anti-platelet endothelial cell adhesion molecule 1 and smooth muscle α-actin antibodies. Vessels are counted on six areas, three on the anterior wall and three on the posterior wall in cross sections of the left ventricle. Area 1 is made up entirely of muscle tissue, area 2 has both muscle and scar, and area 3 has scar only. Vectors are injected into area 2 at the anterior wall. Hence, comparison between the injected areas in the anterior and the corresponding uninjected posterior areas indicates the effect of the agRNA on VEGF expression. Capillary density is expressed as the ratio of capillary to cardiac myocyte for area 1 and as the number of capillaries per $mm^2$ for areas 2 and 3. The density of α-actin-positive vessels is expressed as the number of vessels per $mm^2$ or all areas. Activation of VEGF expression is demonstrated by an increase in capillaries and α-actin-positive vessels in all three areas of the anterior walls compared with the posterior walls in the same hearts and compared with the anterior walls of control groups.

Clinical Trials: The safety and efficacy of VEGF-activating agRNA therapy in humans is evaluated in a clinical study designed after a study described by Losordo et al (2002). Eligible patients include Canadian Cardiovascular Society (CCS) class III or IV angina refractory to maximum medical therapy, multivessel coronary artery disease not suitable for bypass surgery or angioplasty, and reversible ischemia on stress SPECT Tc 99m sestamibi nuclear imaging. Subjects are excluded if they had a previous history or current evidence of malignancy, active diabetic retinopathy, or evidence of severe LV systolic dysfunction (LV ejection fraction [EF] <20% by transthoracic 2D echocardiography).

VEGF-inducing agRNA-expressing vectors are injected into the patients. Subjects undergo nonfluoroscopic LV EMM immediately before injection of the vector to guide injections to foci of ischemic myocardium. Follow-up EMM is performed at 12 weeks after injections. The pre-specified primary efficacy parameters are change from baseline in CCS angina classification and exercise tolerance at the 12-week follow-up visit.

EXAMPLE 4 agRNA-Induced Transcriptional Increase

We reasoned that gene activation could be more readily observed against a low basal level of gene expression. Therefore, to address our hypothesis, we introduced duplex RNAs into MCF-7 cells, a breast cancer cell line with a much lower basal level of PR protein expression than observed in T47D cells (Janowski et al (2006a) Nature Struc. Mol. Biol. 13:787-792; Jenster et al (1997) Proc Natl Acad Sci USA 94:7879-7884).

We initiated testing with RNA PR11, a duplex complementary to the PR promoter sequence from −11 to +8. We chose PR11 because it had not inhibited PR expression in T47D cells but was surrounded by agRNAs that were potent inhibitors. For comparison, we also tested RNAs PR9 and PR26 that we had previously shown to be potent inhibitors of PR expression in T47D cells.

We introduced duplex RNA PR11 into MCF-7 cells using cationic lipid (Janowski et al (2006b) Nature Protocols 1:436-443) and observed an 18-fold increase in levels of PR protein by Western analysis, indicating that agRNAs could produce substantial up-regulation of gene expression when tested in an appropriate cellular context. Addition of PR9 did not affect PR expression, while PR26 yielded a modest 2-fold increase in PR levels. Two siRNAs that were complementary to downstream coding sequences within PR mRNA inhibited expression of PR protein, demonstrating that PR levels could be reduced by standard post-transcriptional silencing in MCF-7 cells.

After observing RNA-mediated activation of gene expression by PR11 we assayed the specificity and potency of the phenomenon. We tested a battery of mismatch and scrambled control duplexes, including mismatches that preserved complementarity at the either end of the duplex. These control duplexes did not increase expression of PR, demonstrating that upregulation was sequence-specific. Addition of PR11 at varied concentrations demonstrated that activation was potent, with 17-fold activation achieved at a 12 nM concentration.

We then re-examined gene activation by duplex RNAs in T47D cells. To facilitate unambiguous observation of activation, we reduced the basal level of PR expression by growing the cells in culture medium containing charcoal-treated serum (Hurd et al (1995) J. Biol. Chem.). As expected, use of serum-stripped media lacking hormones reduced PR expression. Addition of RNA PR11 induced PR expression to levels observed for T47D cells in normal media. These results demonstrate that PR11 has the same physiologic effect in two different breast cancer cell types and that PR11 is able to counteract a well-established mechanism for manipulating hormone receptor expression.

PR protein is expressed as two isoforms, PR-A and PR-B, which play differing roles in physiologic processes (Conneely et al, (2003) Mammary Gland Biol. Neoplasia 8:205-214). The promoter for PR-B is upstream from the promoter for PR-A and the RNAs used in this study target the PR-B promoter. We had previously observed that agRNAs, siRNAs, antisense PNAs, or antigene PNAs that target the PR-B promoter (agRNA, antigene PNA) or PR-B mRNA (siRNA, antisense PNA) also reduce levels of PR-A (Janowski et al, 2005; Janowski et al, 2006a; Janowski et al, 2006b; and Janowski et al (2006c) Nature Chem. Biol 1:210-215) indicating that expression of PR-A is linked to expression of PR-B. We now observe that RNAs targeting the PR-B promoter can also enhance expression of both PR-B and PR-A protein, providing complementary evidence that expression of the isoforms is linked.

To correlate activity with target sequence, we tested a series of duplex RNAs targeted to sequences throughout the region −56 to +17 within the PR promoter. Several of these duplex RNAs induced expression of PR by 5 fold or greater (Table 5). Small shifts in target sequence had large consequences for activation. For example, a single base shift upstream (PR12) or downstream (PR10) from PR11 substantially reduced activation. Experiments were repeated several times with similar results. These data indicate that sequences throughout the promoter are suitable targets and that the requirements for RNA-mediated gene activation are flexible.

TABLE 5

| RNA Targeting PR | Fold Activation Relative to Mismatch Controls |
| --- | --- |
| −2/+17 | 8x |
| −6/+13 | 6x |
| −9/+10 | 7x |
| −10/+9 | 1x |
| −11/+8 | 19x |
| −12/+7 | 3x |
| −13/+6 | 4x |
| −14/+5 | 16x |
| −19/−1 | 7x |
| −22/−3 | 13x |
| −23/−4 | 6x |
| −24/−5 | 3x |
| −25/−6 | 8x |
| −26/−7 | 10x |
| −29/−10 | 6x |
| −39/−20 | 3x |
| −49/−30 | 3x |

We performed order of addition experiments in which inactive RNAs PR10 or PR12 were transfected either before or after transfection with activating RNA PR11 (Table 6). When PR10 or PR12 were added to cells first, we observed that subsequent addition of PR11 did not result in activation. When PR11 was added to cells first, PR10 or PR12 did not block gene activation. These competition assays indicate that inactive RNAs PR10 and PR12 bind at the same target sequence as PR11. Recognition is sufficient to block binding of PR11 and prevent activation of PR expression. Competition of PR11 with PR10 and PR12 further documents the target- and sequence-specificity of RNA-mediated activation of PR.

TABLE 6

| Transfection 1 | Transfection 2 | Outcome |
| --- | --- | --- |
| Activating RNA PR11 | Inactive RNA PR8 | Activation |
| Activating RNA PR11 | Inactive RNA PR12 | Activation |
| Inactive RNA PR12 | Activating RNA PR11 | No Activation |
| Inactive RNA PR8 | Activating RNA PR11 | No Activation |

To determine whether duplex RNAs could activate expression of other genes we examined a series of RNAs targeted to major vault protein (MVP) (Huffman and Corey, (2004) Biochemistry 44:2253-2261). We chose MVP because we previously silenced its expression with agRNAs (Janowski et al, 2005). MVP6 and MVP9 inhibited gene expression, a result that we had reported previously (Janowski et al, 2005). By contrast, MVP35 (corresponding to nucleotides 1819-1837 of Genbank Accession no. AJ238509, GI:583487), MVP54, and MVP82, increased expression by 2-4 fold above normal levels. These data indicate that duplex RNAs can enhance expression of genes with relatively high basal levels of expression, similar to our initial observation of RNA-mediated upregulation of PR in T47D cells.

Quantitative PCR (QPCR) reveals that treatment of MCF-7 cells with PR11 enhances expression of PR mRNA under a variety of cell culture conditions. We had previously shown that inhibition of PR expression in T47D cells by siRNAs (Hardy et al (2006) Mol Endocrinol, Epub ahead of print Jun. 13, 2006) or agRNAs (unpublished) significantly increases expression of cyclooxygenase-2 (COX-2) after induction with interleukin1 beta (IL-113). We now observe that activation of PR gene expression in MCF-7 cells after treatment with RNA PR11 reduces COX-2 expression in the presence or absence of IL-1β. Treatment of cells with PR11 did not alter levels of estrogen receptor-alpha (ER-alpha), a key regulator of PR expression. Accordingly, a specific embodiment of our invention is a method for decreasing Cox-2 expression in a cell by contacting the cell with a polynucleotide oligomer of 12-28 bases complementary to a region located between nucleotides −100 to +25 relative to a transcription start site of the human progesterone receptor (hPR) gene under conditions whereby the oligomer selectively increases synthesis of the hPR; and detecting decreased synthesis of the Cox-2; wherein the oligomer is preferably double-stranded RNA.

Our data demonstrate that activating RNAs can be used to manipulate expression of physiologically-relevant downstream target genes in a predictable manner and that the induced PR is fully functional.

REFERENCES

Akgul et al (2004) Cell. Mol. Life. Sci. 61:2189-2199
Bernstein and Allis (2005) Genes Dev. 19:1635-1655.
Bourdon et al (2005) Genes Dev, 19: 2122-2137
Braasch et al (2003) Biochemistry. 42:7967-75.
Caldas et al (2005) Oncogene 24:1994-2007.
Castanotto et al (2005) Mol. Therapy. 12:179-183.
Czaudema et al (2003) Nucleic Acids Res. 31:2705-16.
Elbashir et al (2001) Nature. 411:494-8.
Elmen et al (2005) Nucleic Acids Res. 33:439-47
Grewal and Moazed (2003) Science 301:798-802.
Haaima et al (1997) Nucleic Acids Res. 25:4639-43
Hahn (2004) Nat Struct Mol Biol. 11:394-403.
Hassani et al (2004) J Gene Med. 7:198-207
Janowski et al (2005) Nature Chem Biol 1:210-216
Janowski et al (2005) Nature Chem Biol 1:216-222.
Kaihatsu et al (2003) Biochemistry. 42:13996-4003
Kaihatsu et al. (2004) Biochemistry 43, 14340-14347
Kawasaki and Taira (2004) Nature 431:211-7.
Kuwabara et al (2004) Cell 116:779-793
Kuwabara et al (2005) Nuc Acid Symp Series 49:87-88
Lamb and Crawford (1986) Mol Cell Biol 6, 1379-1385
Lange et al (2000) Biochem Biophys Res Comm 278:125-133.
Li et al (2005) Proc Amer Assoc Cancer Res 46:6105
Massenegger et al (1994) Cell 76:567-576.
Matzke et al. (2004) Biochem. Biophys. Acta 1677, 129-141.
Morris et al (2004) Science 305:1289-92.
Nielsen (2004) Mol. Biotechnol. 26:233-48
Park et al (2004) Biochem. Biophys. Res. Comm. 323:275-280.
Paroo and Corey (2004) Trends Biotechnol. 22:390-4.
Pelissier and Wassenegger (2000) RNA 6:55-65.
Rohaly et al. (2005) Cell, 122, 21-32.
Schramke et al (2005) Nature 435:1275-1279
Sharrard and Maitland (2000) Biochim Biophys Acta 1494: 282-285.
Sigova et al (2004) Genes Dev. 18:2359-2367.
Su et al (2002) Proc. Natl. Acad. Sci. USA 99:9480-9485
Su et al (2004). Proc. Natl. Acad. Sci. USA 101:16280-16285.
Sugiyama et al (2005) Proc. Natl. Acad. Sci. USA 102:152-157.
Summerton and Weller (1997) Antisense Nucleic Acid Drug Dev. 7:187-95
Svoboda, P. et al (2004) Nucl. Acids. Res. 32:3601-3606.
Takai and Jones (2002) Proc Natl Acad Sci USA. 99:3740-5

Takai and Jones (2003) In Silico Biol. 3:235-40.
Tang (2004) Trends Biochem. Sci. 30:106-114.
Ting et al (2005) Nat. Genet. 37:906-10.
Tischer et al (1991) J Biol. Chem. 266:11947-54
Tyler et al (1999) PNAS 96:7053-7058
Urban-Klein et al (2005) Gene Ther. 12:461-6.

Verdel et al (2003) Science 303:672-676.
Volpe et al (2002) Science 297:1833-1837.
Wahlestedt et al (2000) Proc. Natl. Acad. Sci. USA, 97: 5633-5638.
Zender et al (2003) Proc. Natl. Acad. Sci USA 100:7797-802

---

What is claimed is:

1. A method of selectively increasing synthesis of a target transcript of a human major vault protein (hMVP) gene, a E-cadherin gene, a p53 gene, or a PTEN gene in a mammalian cell, the method comprising the steps of:
    contacting the cell with a polynucleotide oligomer of 12-28 bases complementary to a region within a target promoter of the gene under conditions whereby the oligomer selectively increases synthesis of the target transcript; and
    detecting resultant selective increased synthesis of the target gene;
wherein the oligomer is double-stranded RNA, and wherein the oligomer is selected from the group consisting of SEQ ID NOS 1-3 and 7-18.

2. The method of claim 1, wherein the region is located between nucleotides −50 to +25 relative to a transcription start site of the gene.

3. The method of claim 1, wherein the region is located between nucleotides −30 to +17 relative to a transcription start site of the gene.

4. The method of claim 1, wherein the region includes a transcription start site of the gene.

5. The method of claim 1, wherein the target promoter is the promoter of the target transcript.

6. The method of claim 1, wherein the target promoter is the promoter of an isoform of the target transcript.

7. The method of claim 1, wherein the target promoter is the promoter of an predetermined isoform of the target transcript, and synthesis of the isoform is inhibited.

8. The method of claim 1, wherein the target promoter is both the promoter of the target transcript and the promoter of an isoform of the target transcript.

9. The method of claim 1, wherein the oligomer is double-stranded RNA of 18-25 bases.

10. The method of claim 1, wherein the oligomer comprises a nucleotide having a 2' chemical modification.

11. The method of claim 1, wherein the oligomer comprises a serum stability-enhancing chemical modification selected from the group consisting of a phosphorothioate internucleotide linkage, a 2'-O-methyl ribonucleotide, a 2'-deoxy-2'-fluoro ribonucleotide, a 2'deoxy ribonucleotide, a universal base nucleotide, a 5-C-methyl nucleotide, an inverted deoxyabasic residue incorporation, and a locked nucleic acid.

12. The method of claim 1, wherein the cell is a cultured cell in vitro.

13. The method of claim 1, wherein the cell is in situ in a host.

14. The method of claim 1, wherein the contacting step is free of viral transduction.

15. The method of claim 1, wherein the contacting step is free of viral transduction, and the cell is contacted with a composition consisting essentially of the oligomer.

16. The method of claim 1, wherein the contacting step is free of viral transduction, and there is at least a 2-fold resultant increased synthesis of the target transcript.

17. The method of claim 1, wherein the oligomer is a double-stranded RNA of 18-25 bases, a single region of the target promoter is targeted, and there is at least a 2-fold resultant increased synthesis of the target transcript.

18. The method of claim 1, wherein the cell is contacted with a 1-100 nanomolar concentration of the oligomer.

19. The method of claim 1, wherein the cell is a cancer cell.

* * * * *

SEQUENCE LISTING

```
<160> NUMBER OF SEQ ID NOS: 37

<210> SEQ ID NO 1
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 1
ugggcuuggc cugccuugc                                                  19

<210> SEQ ID NO 2
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 2
gggcccuuua acucccaag                                                  19

<210> SEQ ID NO 3
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 3
cccccucuca guggcgucg                                                  19

<210> SEQ ID NO 4
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 4
ggcguuguua gaaagcugu                                                  19

<210> SEQ ID NO 5
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 5
aggaggcguu guuagaaag                                                  19

<210> SEQ ID NO 6
<211> LENGTH: 19
<212> TYPE: RNA
<213> ORGANISM: artificial
<220> FEATURE:
<223> OTHER INFORMATION: antigene RNA polynucleotide oligomer
```

```
<400> SEQUENCE: 6
agaggaggag gcguuguua                                                    19

<210> SEQ ID NO 7
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 7
gcuaaaaguu uugagcuuc                                                    19

<210> SEQ ID NO 8
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 8
aaaguuuuga gcuucucaa                                                    19

<210> SEQ ID NO 9
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 9
aguuuugagc uucucaaaa                                                    19

<210> SEQ ID NO 10
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 10
cgcgacugcg cucaguucu                                                    19

<210> SEQ ID NO 11
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 11
acugcgcuca guucucucc                                                    19

<210> SEQ ID NO 12
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 12
ugcgcucagu ucucuccuc                                                    19

<210> SEQ ID NO 13
<211> LENGTH: 19
<212> TYPE: RNA
```

```
<213> ORGANISM: artificial
<220> FEATURE:
<223> OTHER INFORMATION: antigene RNA polynucleotide oligomer

<400> SEQUENCE: 13
ugacucugca cccuccucc                                                    19

<210> SEQ ID NO 14
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 14
ucugcacccu ccucccaa                                                     19

<210> SEQ ID NO 15
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 15
ugcacccucc uccccaacu                                                    19

<210> SEQ ID NO 16
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 16
auuacuugcc cuuacuugu                                                    19

<210> SEQ ID NO 17
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 17
cuugcccuua cuugucaug                                                    19

<210> SEQ ID NO 18
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 18
ugcccuuacu ugucauggc                                                    19

<210> SEQ ID NO 19
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 19
gaucgcggag gcuuggggc                                                    19
```

<210> SEQ ID NO 20
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 20
ggaggaucgc ggaggcuug					19

<210> SEQ ID NO 21
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 21
gggaggaucg cggaggcuu					19

<210> SEQ ID NO 22
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 22
ggggaggauc gcggaggcu					19

<210> SEQ ID NO 23
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 23
cggggaggau cgcggaggc					19

<210> SEQ ID NO 24
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 24
gcggggagga ucgcggagg					19

<210> SEQ ID NO 25
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 25
agcggggagg aucgcggag					19

<210> SEQ ID NO 26
<211> LENGTH: 19
<212> TYPE: RNA
<213> ORGANISM: artificial
<220> FEATURE:
<223> OTHER INFORMATION: antigene RNA polynucleotide oligomer -continued

```
<400> SEQUENCE: 26
uagcggggag gaucgcgga                                                19

<210> SEQ ID NO 27
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 27
guagcgggga ggaucgcgg                                                19

<210> SEQ ID NO 28
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 28
gguagcgggg aggaucgcg                                                19

<210> SEQ ID NO 29
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 29
ugguagcggg gaggaucgc                                                19

<210> SEQ ID NO 30
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 30
ucggcuggua gcggggagg                                                19

<210> SEQ ID NO 31
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 31
aaaagucggc ugguagcgg                                                19

<210> SEQ ID NO 32
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 32
uaaaagucgg cugguagcg                                                19

<210> SEQ ID NO 33
<211> LENGTH: 19
<212> TYPE: RNA
```

```
<213> ORGANISM: artificial
<220> FEATURE:
<223> OTHER INFORMATION: antigene RNA polynucleotide oligomer

<400> SEQUENCE: 33
uuuuuaaaag ucggcuggu                                              19

<210> SEQ ID NO 34
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 34
uuuuuuuuuu aaaagucgg                                              19

<210> SEQ ID NO 35
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 35
cccccuuuuu uuuuuaaaa                                              19

<210> SEQ ID NO 36
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 36 cgccccccc uuuuuuuu                                                19

<210> SEQ ID NO 37
<211> LENGTH: 19
<212> TYPE: RNA
<213> ORGANISM: artificial
<220> FEATURE:
<223> OTHER INFORMATION: antigene RNA polynucleotide oligomer

<400> SEQUENCE: 37
caugcgcccc ccccuuuuu                                              19
```